US012758386B2

(12) United States Patent
Jagger et al.

(10) Patent No.: US 12,758,386 B2
(45) Date of Patent: Oct. 13, 2026

(54) APPARATUS AND METHOD OF PREPARING BONE FIBERS

(71) Applicant: RTI SURGICAL, INC., Alachua, FL (US)

(72) Inventors: Karl Jagger, Excelsior, MN (US); Jeff Bossert, Gainesville, FL (US); Bently Robinson, Gainesville, FL (US); Jonathan Nath, Inver Grove Heights, MN (US); Brian Beaubien, St. Paul, MN (US); Jake Elliott, Gainesville, FL (US)

( * ) Notice: Subject to any disclaimer, the term of this patent is extended or adjusted under 35 U.S.C. 154(b) by 208 days.

(21) Appl. No.: 18/274,190

(22) PCT Filed: Jan. 25, 2022

(86) PCT No.: PCT/US2022/013773

§ 371 (c)(1),
(2) Date: Jul. 25, 2023

(87) PCT Pub. No.: WO2022/159913

PCT Pub. Date: Jul. 28, 2022

(65) Prior Publication Data

US 2024/0082002 A1 Mar. 14, 2024

Related U.S. Application Data

(60) Provisional application No. 63/141,404, filed on Jan. 25, 2021.

(51) Int. Cl.

*A61F 2/28* (2006.01)
*A61L 27/36* (2006.01)
*B02C 1/00* (2006.01)

(52) U.S. Cl.

CPC ............ *A61F 2/28* (2013.01); *A61L 27/3608* (2013.01); *A61L 27/365* (2013.01); *A61L 27/3683* (2013.01); *A61L 2430/02* (2013.01)

(58) Field of Classification Search

CPC ................ A61F 2/28; A61F 2002/4645; A61F 2002/4644; A61F 2002/2835; A61L 27/3608; A61L 27/365; A61L 27/3683; A61L 27/3695; A61L 2430/02; B02C 19/10; B02C 1/00; B02C 1/12; B02C 1/18; B02C 1/02; B02C 1/36

USPC ...................................................... 606/86, 87

See application file for complete search history.

(56) References Cited

U.S. PATENT DOCUMENTS

| | | | | | |
|---|---|---|---|---|---|
| 10,258,201 | B1 * | 4/2019 | Rasekhi | B02C 19/20 | |
| 11,166,831 | B2 * | 11/2021 | Myint | A61L 27/365 | |
| 2002/0120347 | A1 * | 8/2002 | Boyer, II | A61B 17/7071 | 623/23.51 |

(Continued)

*Primary Examiner* — Jessica Weiss

(74) *Attorney, Agent, or Firm* — Skaar Ulbrich Macari, P.A.

(57) ABSTRACT

A fiber producing apparatus and method for producing fibers having at least two different dimensions or characteristics. The apparatus cuts fibers of varying length, thickness, and width by varying a cutting stroke length, using a cutting plate having different cutting blades, and applying varying pressure on a material during the cutting process. The fibers of the present invention are moldable and can be used as an implant having a structure that mimics native or natural bones. The ability to mimic natural bone improves cellular infiltration and bone growth.

20 Claims, 17 Drawing Sheets

(56) References Cited

U.S. PATENT DOCUMENTS

| | | | | |
|---|---|---|---|---|
| 2007/0164137 | A1* | 7/2007 | Rasekhi | A61F 2/4644 241/92 |
| 2013/0268075 | A1* | 10/2013 | McKay | A61F 2/4465 623/17.16 |
| 2014/0061343 | A1* | 3/2014 | Waibel | A47J 43/25 241/95 |
| 2014/0314822 | A1* | 10/2014 | Carter | A61L 27/3608 264/28 |
| 2015/0245925 | A1* | 9/2015 | Willyerd | B02C 18/144 241/28 |
| 2017/0266348 | A1* | 9/2017 | Gaskins | A61L 27/3821 |
| 2018/0221174 | A1* | 8/2018 | Meade | A61F 2/4644 |
| 2018/0263779 | A1* | 9/2018 | Scarborough | A61F 2/28 |
| 2021/0106438 | A1* | 4/2021 | Myint | A61B 17/1635 |
| 2022/0105242 | A1* | 4/2022 | Carter | A61L 27/3608 |

* cited by examiner

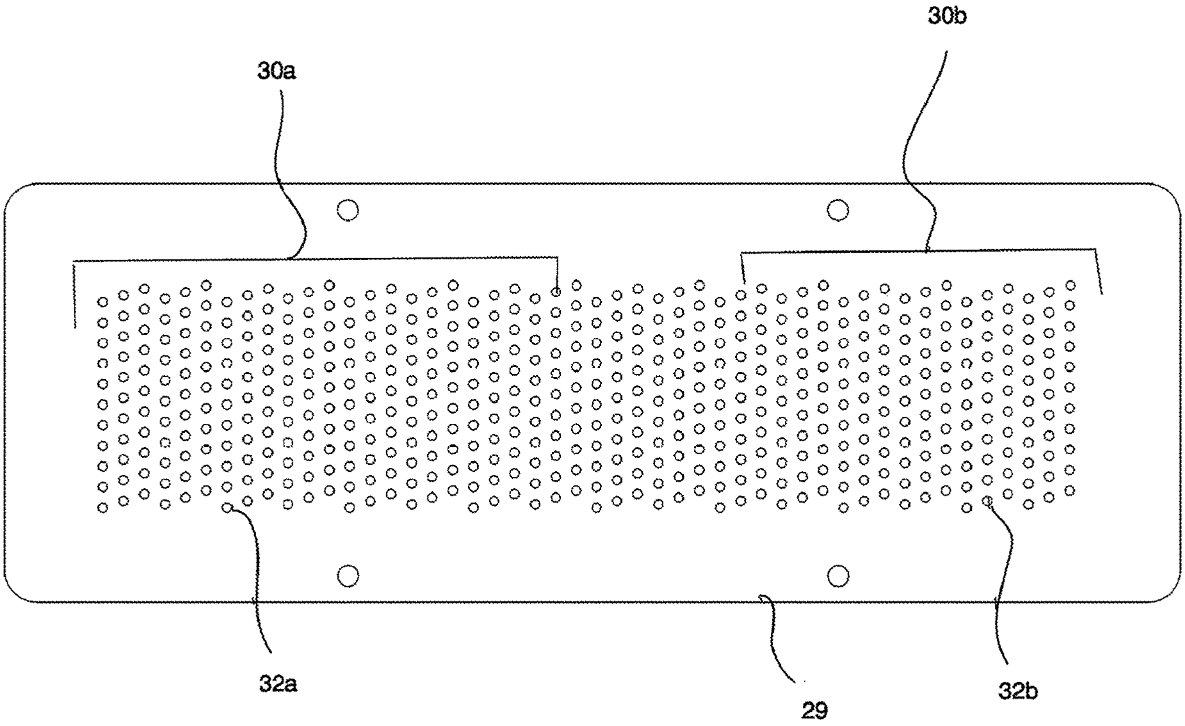
FIG. 4A
FIG. 4B
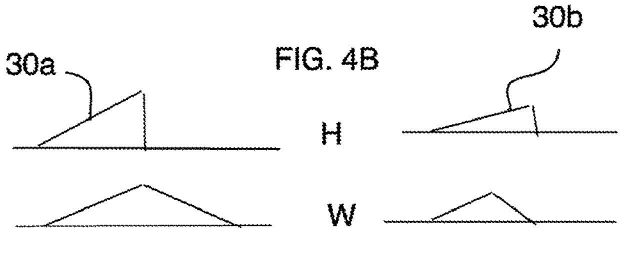

APPARATUS AND METHOD OF PREPARING BONE FIBERS

CROSS REFERENCE

This application claims the benefit of priority from U.S. Provisional Application No. 63/141,404, filed Jan. 25, 2021, titled "APPARATUS AND METHOD OF PREPARING BONE FIBERS," the entire contents of which are hereby incorporated by reference herein.

FIELD

The present invention relates to a bone fiber composition having a varying physical characteristic and to an apparatus and method for preparing a bone fiber composition having a varying physical characteristic. More particularly, the present invention includes a bone fiber composition having at least different lengths, widths, and/or thickness, and to an apparatus capable of producing a bone fiber composition having at least different lengths, widths, and/or thickness.

BACKGROUND

The present invention is directed to the field of biocompatible materials for use in forming or filling voids, and voids in devices, for implantation in animals and humans. More particularly, the present invention is directed to an implantable tissue graft/implant formed from an allogeneic biocompatible human bone that is capable of being formed into a variety of tissue implants or compositions having different properties and different shapes. The present invention is useful because it provides a fiber composition that is easily transportable and stored. The fiber composition is then able to be formed by a surgeon into an implantable device, composition, or structure, having a conformable shape that is versatile in its ability to be formulated into a variety of implants or grafts that can be used in the treatment of a variety of medical conditions patients.

Conventional treatments for bone defects caused by various types of injuries or congenital abnormalities include the use of biocompatible on-organic materials and biocompatible organic materials. Non-organic materials include devices, materials and compositions made from metals such as titanium, or materials such as ceramics and polypropylene. A shortcoming of such non-organic devices includes an incompatibility between the non-organic device properties and the host tissue, which causes the non-organic device to loosen at the interface between the host tissue and the non-organic device. Additionally, it is common for non-organic devices to become encapsulated by the host tissue, which increases the risk of infection and rejection.

One solution to the above identified problems was the use organic materials in place of or in combination with metal, ceramic, or polypropylene implants. The use of organic materials include the use of allograft bone material. Under the proper conditions, and under the influence of osteogenic substances, implants made of allograft bone can act as the scaffolding for remodeling by the host's body. These organic implants have the benefit of functioning both structurally and biologically similar to the host tissue. Further, they allow cellular recruitment through the natural openings and proteins present in the bone matrix and allow the graft to be replaced by natural host bone.

While allograft bone fibers are very useful, they have traditionally been made by processes that create shortcomings in their final product. For instance, allograft bone fibers are generally made by using grinders or shredders that create fibers or powders having generally uniform characteristics (e.g., length, width, and thickness). The uniformity is dissimilar to naturally occurring collagen fibers present along the long axis of cortical bone.

It is an object of the present invention to have a novel composition and an apparatus, and method of preparing an allograft bone fiber having varying characteristics that can be formed into an implant or combined with a with improved cellular in-growth properties.

SUMMARY

The applicants have discovered a novel device, apparatus, system, and process of making biocompatible, moldable, allograft material that is formable into an implant having enhanced surface area and entanglement properties for improved cellular infiltration. The present invention provides for an improved composition, device, apparatus, system, and method or process of making implantable materials for use in tissue regeneration in animals and humans. The apparatus of the present invention can manually and/or automatically convert allograft donor bone material into a fiber or shaving composition having at least two different characteristics, including having at least two different lengths, widths, and/or thickness. For example, the fibers of the composition can have at least two different lengths and at least two different widths, or it can have at least two different lengths and at least two different thicknesses. The present invention contemplates any configuration of fiber formation that includes at least two different characteristics.

In another aspect, the present invention is directed to a device, apparatus, system, and process of making an allograft bone fiber composition having at least two different characteristics that can be combined with an aqueous carrier to create a formable/moldable material. The formable/moldable material can then be implanted or combined with another material or device and then implanted into a patient. Alternatively, the fiber composition of the present invention can be combined with an aqueous carrier formed into an implantable structure or device and then dried into a predetermined shape for implantation. The shape of the tissue graft/implant of the present invention includes a strip, a sheet, a disc, a molded 3D shaped object, a plug, and a wedge.

Ideally, any cortical human bone will be suitable for use in the formation of the fiber composition of the present invention, including at least portions of all the long bones of the human body. Preferably, although not exclusively, the compact portion of the diaphysis of the human long bone.

Prior to the processing of any donor bone material in the device of the present invention, the donor bone material is debrided and washed to remove connective tissue, lipids, blood, and other non-bone tissues. The bone is subsequently demineralized in acid (such as hydrochloric acid or acetic acid). The demineralized bone is then processed by a fiber production apparatus that creates fibers having at least two different characteristics. After the fibers are produced, they undergo acid neutralization and further washing steps to remove any remaining residual non-bone tissues. The fibers are then freeze-dried and packaged into a final vial or jar for distribution to the end-user.

Any of the compositions of tissue graft/implants of the present invention may include collagen fibers, growth factors, antibiotics, cells, or particles such as demineralized bone matrix (DBM), mineralized bone matrix, cortical cancellous chips (CCC), crushed cancellous chips, tricalcium phosphate, hydroxyapatite, or biphasic calcium phosphate (wherein the latter is the combination of tricalcium phosphate and hydroxyapatite) or a combination thereof.

The fiber composition of the present invention, either alone or in a composition, is particularly suited for treating bone trauma, bone disease, bone defects, artificial arthrodesis, or for other treatments where new bone formation and/or repair of bony defects is desired. The fiber composition may be completely or partially demineralized and may be combined with other forms of demineralized bone matrix ("DBM"), mineralized bone matrix, CCC, crushed cancellous chips, tricalcium phosphate, hydroxyapatite, or biphasic calcium phosphate dispersed in the matrix.

The fiber composition of the present invention, either alone or in a mixture, is advantageous because it can be formed/molded, and the resulting shape implanted. The molded implantable material is porous and has a significant surface area and fiber entanglement that tis particularly well suited for the infiltration by colonizing cells (e.g., osteoconduction). The structure of the molded or implanted fiber composition can also be used for the storage and release of materials such as seeded cells, growth factors, and chemotactic agents to attract desired cells (e.g., osteoinduction), including proteins natively present and bound to the bone matrix, such as bone morphogenetic proteins (BMP's).

When the fiber composition or implant of the present invention is to be used to treat bone trauma, disease and defects, artificial arthrodesis and for other treatment where new bone formation is desired, it is optionally seeded with osteogenic cells. Optionally, the fiber composition or implant of the present invention is seeded with stem cells that will provide a natural distribution of the native cells necessary for restoration of the injury or defect at the site of implantation.

The fiber composition, and implants made therefrom, exhibit a great degree of tensile strength. They are readily stitchable and retain most of their tensile strength, even when rehydrated. In addition, upon hydration, the fiber composition and implants of the present invention are moldable and suitable for filling in irregular gaps or holes in the tissue to be repaired. Typically, the hydrated fibers of the composition are press-fitted by a surgeon into the defect or cavity to be filled.

It is also within the scope of the present invention that the fiber composition and the implants made therefrom can be utilized with a load-bearing member used in a spinal fusion. Suitable load bearing members include hollow spinal cages, hollow dowels, C-shaped and D-shaped spacers, and other devices known in the art, having a pocket, chamber, or other mechanism for retaining the bone fibers or molded implant of the present invention. Typically, the load-bearing member has a compressive strength of at least about 1,000 N. More typically, when utilized between lumbar vertebrae, the load-bearing member has a compressive strength of 3,000 to 11,000 N. When utilized between cervical vertebrae, the load bearing member has a compressive strength of about 1,000 to 3,000 N. Suitable load bearing members are known in the art and described in multiple U.S. patents, including, for example in U.S. Pat. Nos. 5,522,899, 5,785,710, 5,776,199 and 5,814,084, 6,033,438, 6,096,081, each of which is hereby incorporated by reference in its entirety The method of making a composition of fibers having varying lengths, widths and/or thicknesses that are suitable for forming implants of improved porosity, surface area, and cell infusion comprises the steps of: obtaining a donor material. The donor bone material is then debrided and washed to remove connective tissue, lipids, blood, and other non-bone tissues. The bone is subsequently demineralized in acid (such as hydrochloric acid or acetic acid). The demineralized bone is then placed in a fiber production apparatus to produce fibers of the present invention. After the fibers are produced, they undergo acid neutralization and further washing steps to remove any remaining residual non-bone tissues. The fibers are then freeze-dried and packaged into a final vial or jar for distribution to the end-user.

In the above method, the matrix of allogeneic human bone comprises from about 1% to about 100% of the final weight of the composition or implant, more typically, from 50% to about 99% of the final weight of the implant, even more typically from 75% to about 99% of the final weight of the implant.

The fibers of the composition can be placed into a jar or vial and transported and stored until needed. The fibers are then able to be combined with an aqueous material/solution to create a formable/moldable mass that can be formed into any desired shape or configuration.

Prior to being used for implantation, the freeze-dried fiber composition of the present invention is removed from its sterile packaging and rehydrated by contacting it with an aqueous material/solution such as water, saline, blood, plasma, a buffered solution, or any other suitable liquid. The rehydrating liquid can also contain a growth factor, or a chemotactic agent as discussed above.

Alternatively, the fiber composition and the aqueous material can be made into a slurry that is an implantable tissue matrix of any size or shape. The slurry can be combined with other agents, such as DBM, CCC or a collagen (e.g., bone, tendon/ligament, fascia, and dermis) slurry before being placed into a mold. In one example embodiment, the slurry can be formed in an implantable film by applying a thin layer of the slurry into/on a flat plate that is allowed to either air dry, air dried with positive airflow, or dried in an oven, preferably a convection oven. The slurry can also be used to produce a sponge, a gasket, or any implantable shape. The slurry (neat or amended) is cast into a mold of the appropriate or desired shape, frozen or dried (to retain its size), and lyophilized. The resulting dried implantable film or shape is then ready for packaging and sterilization.

The above summary is not intended to limit the scope of the invention, or describe each embodiment, aspect, implementation, feature, or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 4A is a top view of a fiber cutting plate for a fiber producing apparatus that is configured to make fibers having at least two-dimensional characteristics.

FIG. 4B is a side view of a different cutting blades of the fiber cutting plate for a fiber producing apparatus that is configured to make fibers having at least two-dimensional characteristics.

Figure 1A:
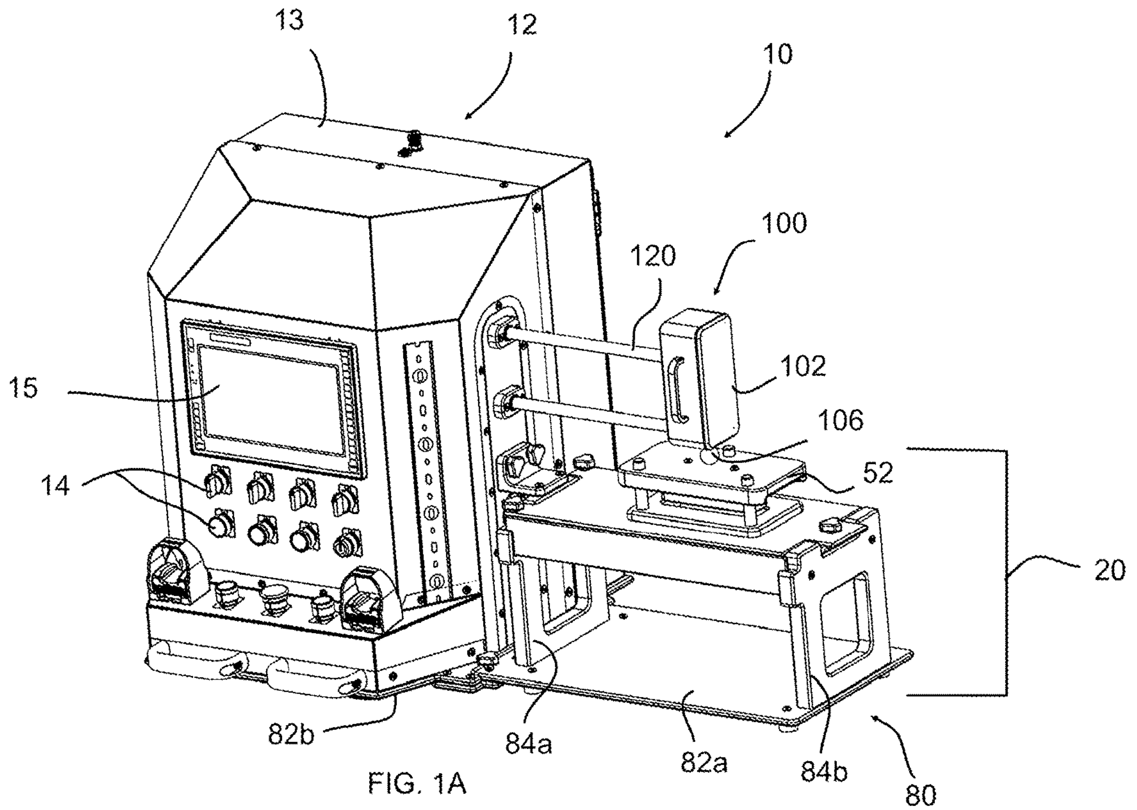
FIG. 1A is a perspective view of a fiber producing apparatus that is configured to make fibers having at least two-dimensional characteristics.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Dimensions and relative proportions of components are merely example embodiments and can be varied unless specifically limited in a given claim. Thus, the dimensions can be varied without departing from the scope of the invention.

The present invention of a fiber producing apparatus 10 that is configured for producing a fiber composition having varying characteristics. In one example embodiment, the fiber producing apparatus 10 is configured to produce a composition of fibers having that at least two-dimensional characteristics such as different lengths and different widths, different lengths and different thicknesses, or different widths and different thicknesses.

In the present invention, the term "fiber composition" refers to fibers having different physical characteristics, such as different lengths and different widths, different lengths and different thicknesses, or different widths and different thicknesses, and the like.

The apparatus, device or system 10 comprises an actuator assembly 12 that controls the production of the fiber composition, a carriage assembly 20 that is configured for holding a donor bone material that is used to produce the fiber composition, a drive assembly 60 that is operatively coupled to and extends between the actuator assembly 12 and the carriage assembly 20, and a support assembly 80 that is configured to support the actuator assembly 12, carriage assembly 20, and the drive assembly 60. The following specification describes example embodiments of the present invention that includes one or more of the above assemblies.

Figure 1B:
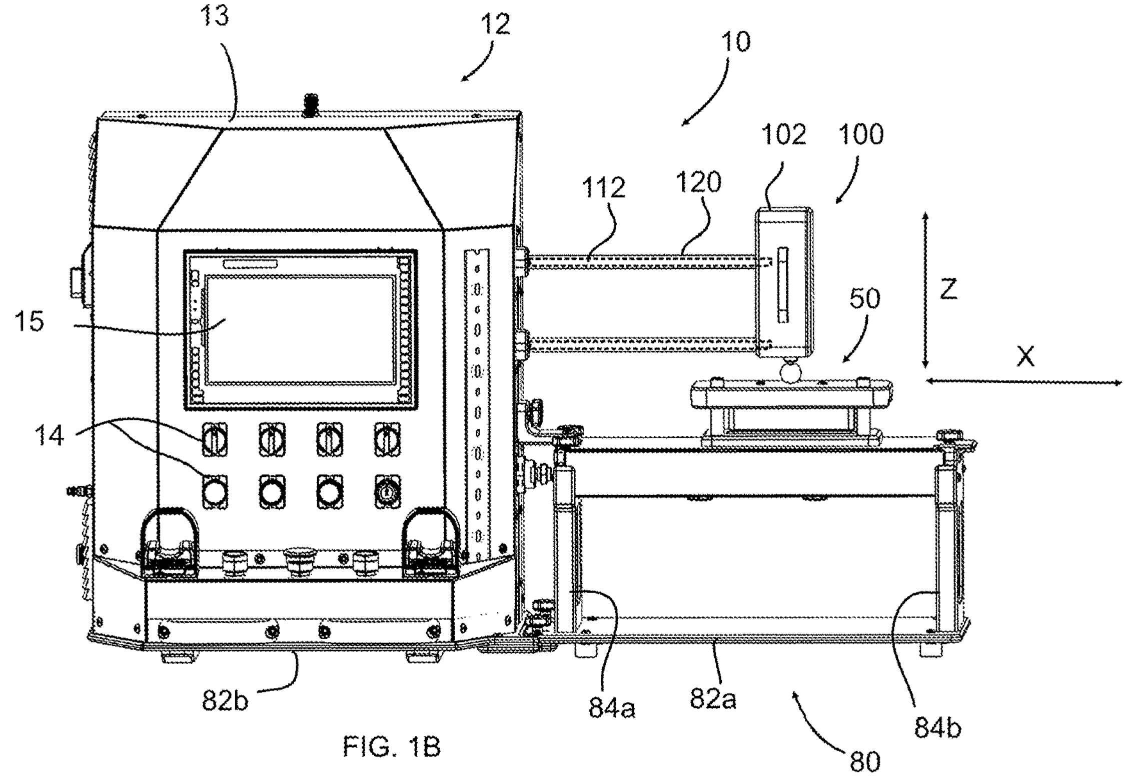
FIG. 1B is a front view of the fiber producing apparatus that is configured to make fibers having at least two-dimensional characteristics.

As illustrated in FIGS. 1A and 1B, the actuator assembly 12 comprises a housing 13 having one or more controls 14 that are configured to change one or more operating parameters of the apparatus 10. By changing or more of the operating parameters, an operator can alter one or more physical characteristics of the fiber composition being produced. The one or more controls 14 permit an operator to change or set an amount of production time, a thickness of a donor tissue being processed, a speed of production, an amount of weight to be used during production, and an amount/weight/volume of fibers to be produced. By changing one or more of the operating parameters, the operator can change/set a length, width, and thickness of the fibers.

In one example embodiment, the housing 13 can also include a display screen 15 that is able to display various operating parameters to an operator, including but not limited to a length, width, and thickness of the fibers being produced, an amount of production time remaining, a thickness of a donor tissue being processed, a speed of production, an amount of weight being used during production, and an amount/weight/volume of fibers produced. It should be appreciated that other production parameters/characteristics can also be displayed, and the above list should not be considered limiting. The housing 13 also includes an interior that is configured to at least hold a portion of a drive assembly 60, which is discussed in more detail below.

Figure 2A:
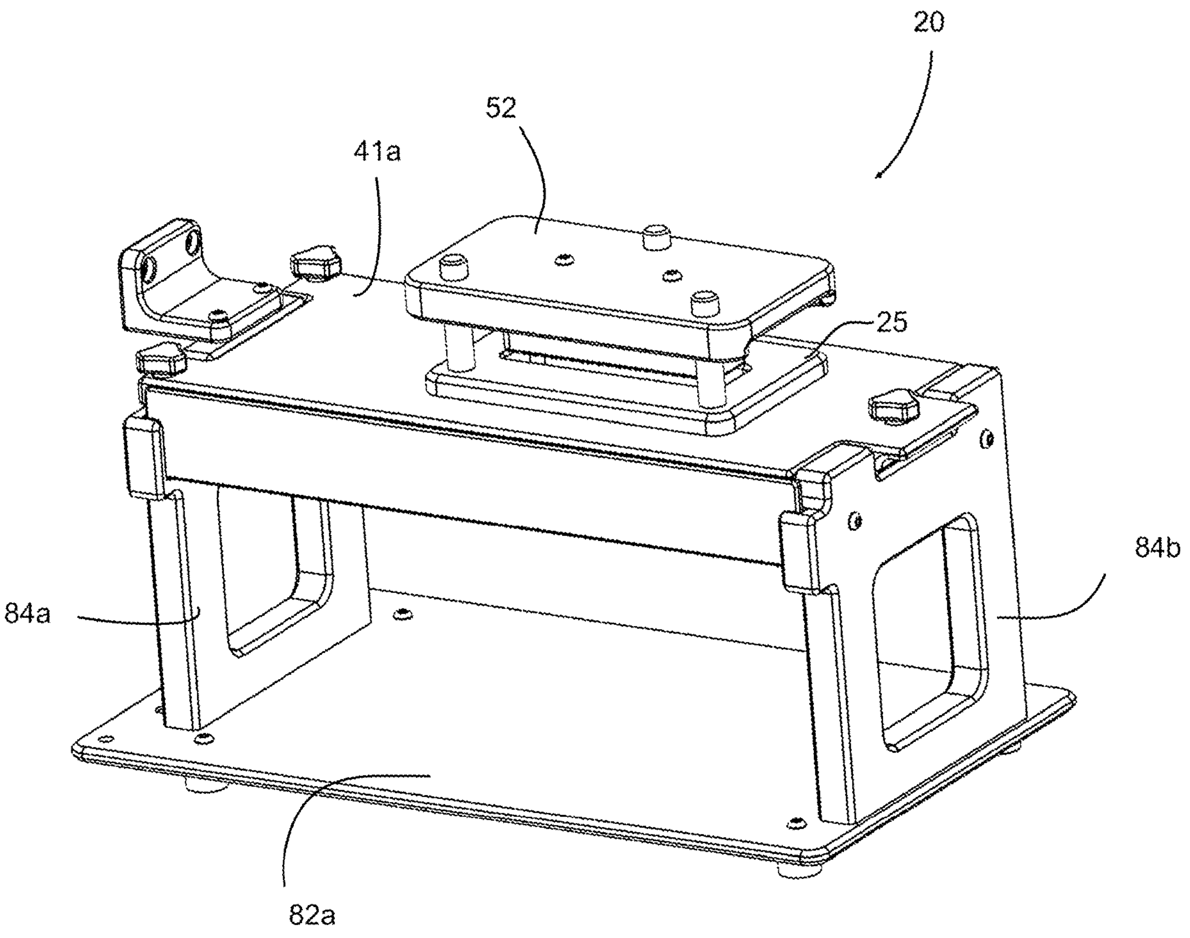
FIG. 2A is a perspective view of a carriage and support assembly for a fiber producing apparatus that is configured to make fibers having at least two-dimensional characteristics.
Figure 2B:
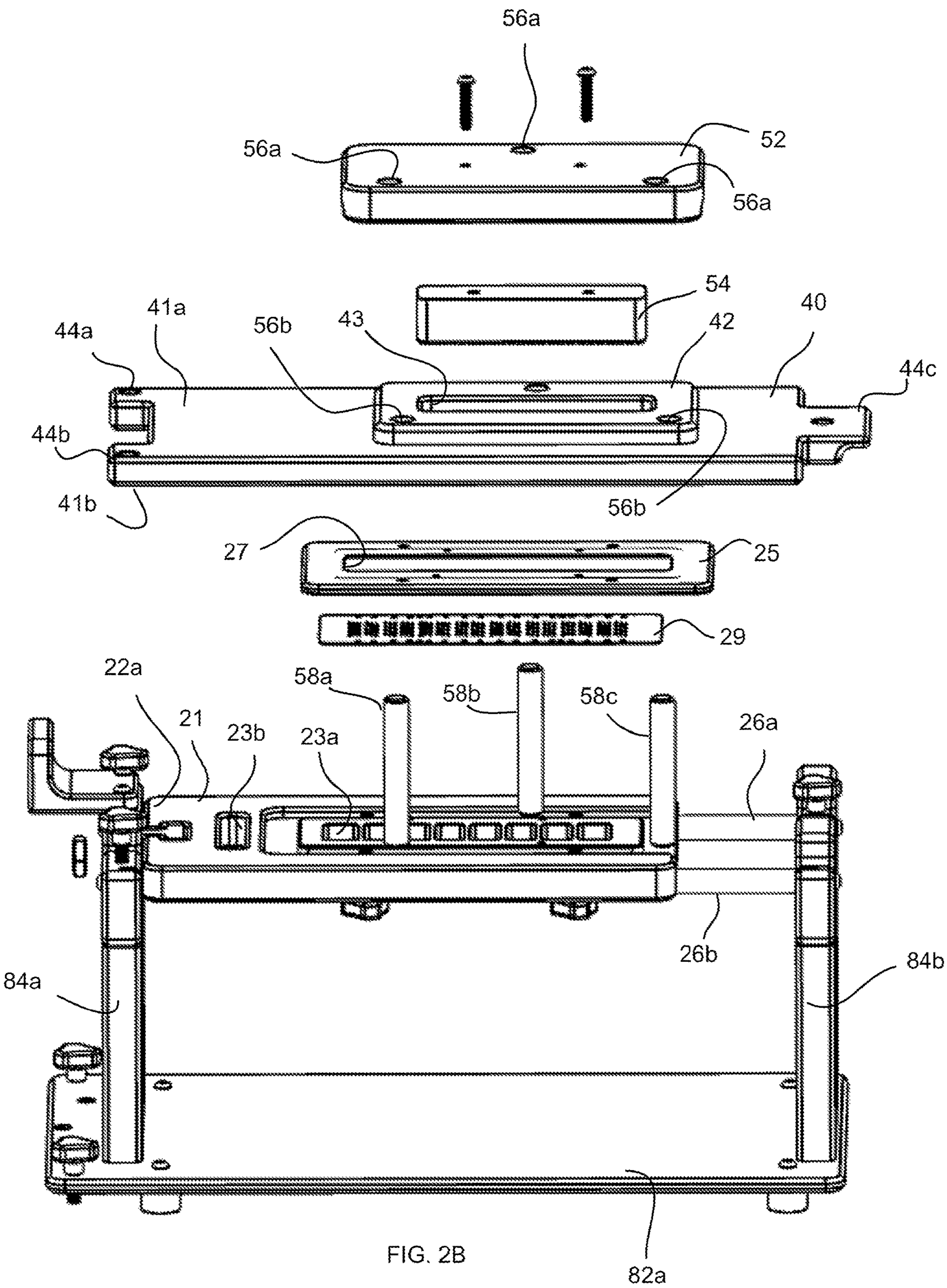
FIG. 2B is an exploded view of a carriage and support assembly for a fiber producing apparatus that is configured to make fibers having at least two-dimensional characteristics.
Figure 3A:
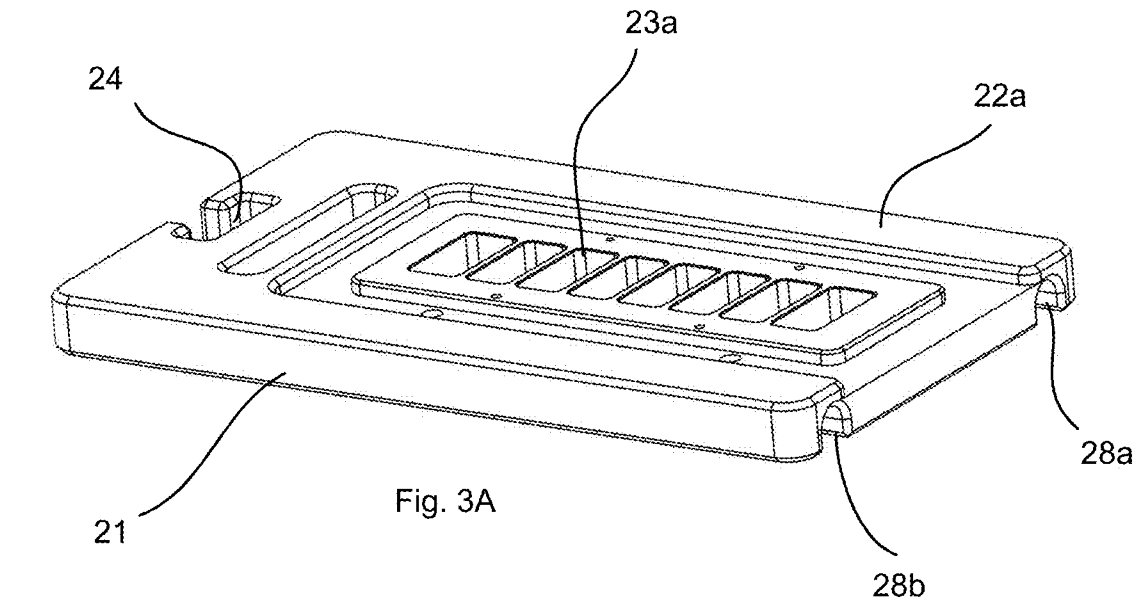
FIGS. 3A-3D are various views of a carriage assembly having a cutting blade for a fiber producing apparatus that is configured to make fibers having at least two-dimensional characteristics.
Figure 3B:
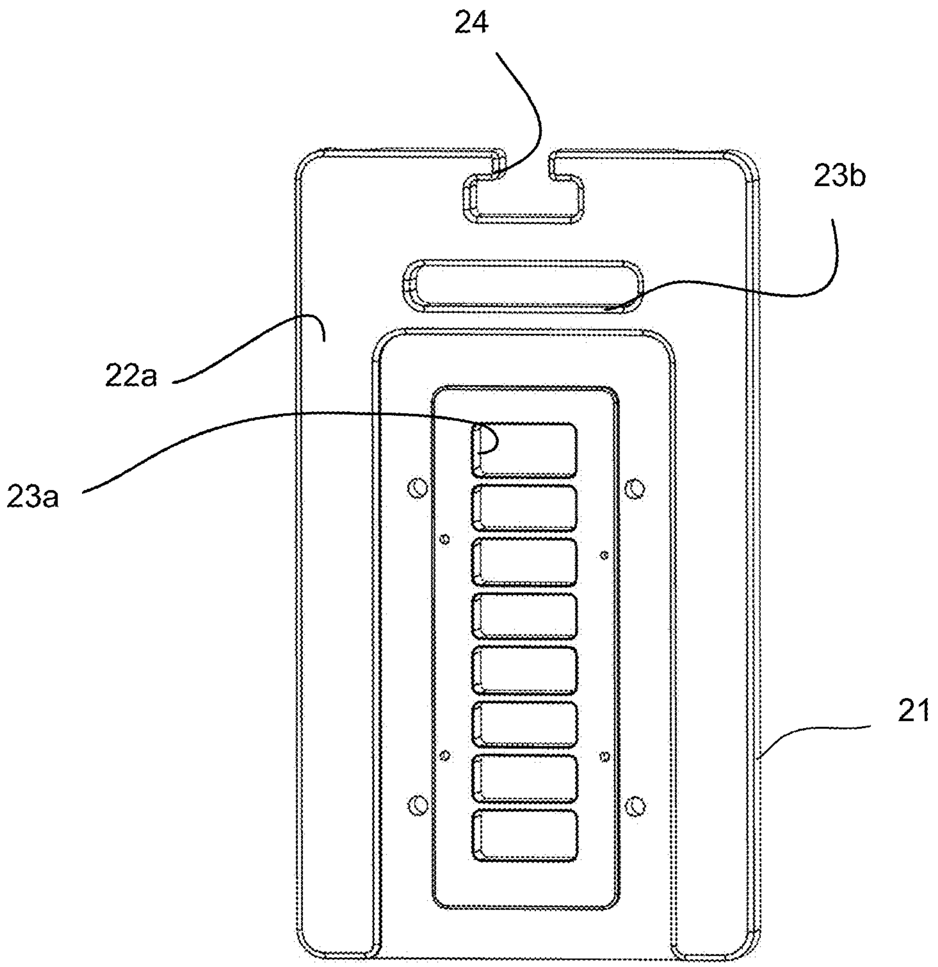
Figure 3C:
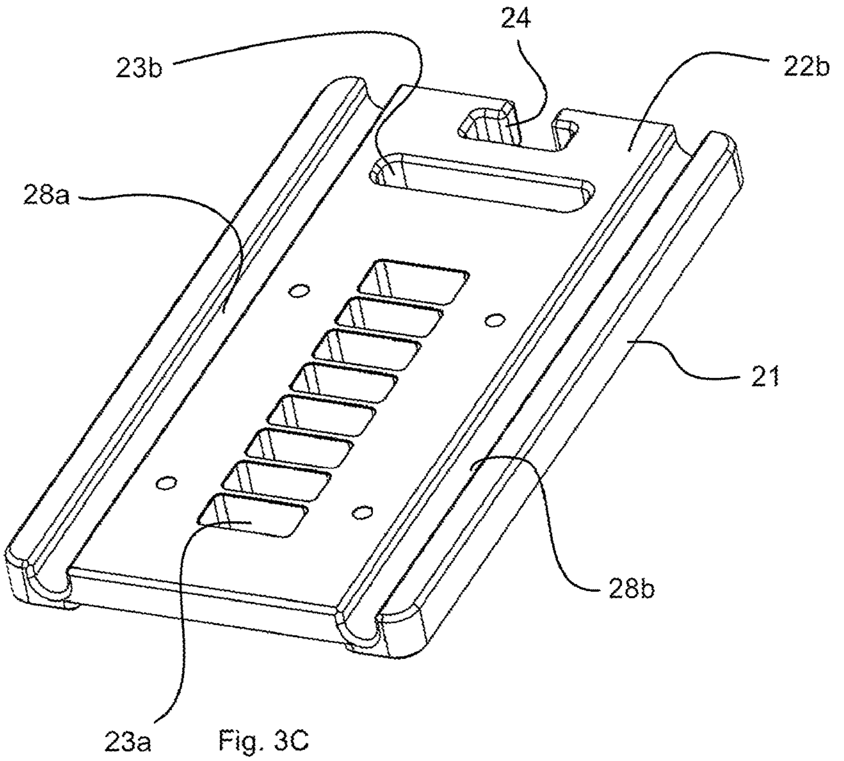
Figure 3D:
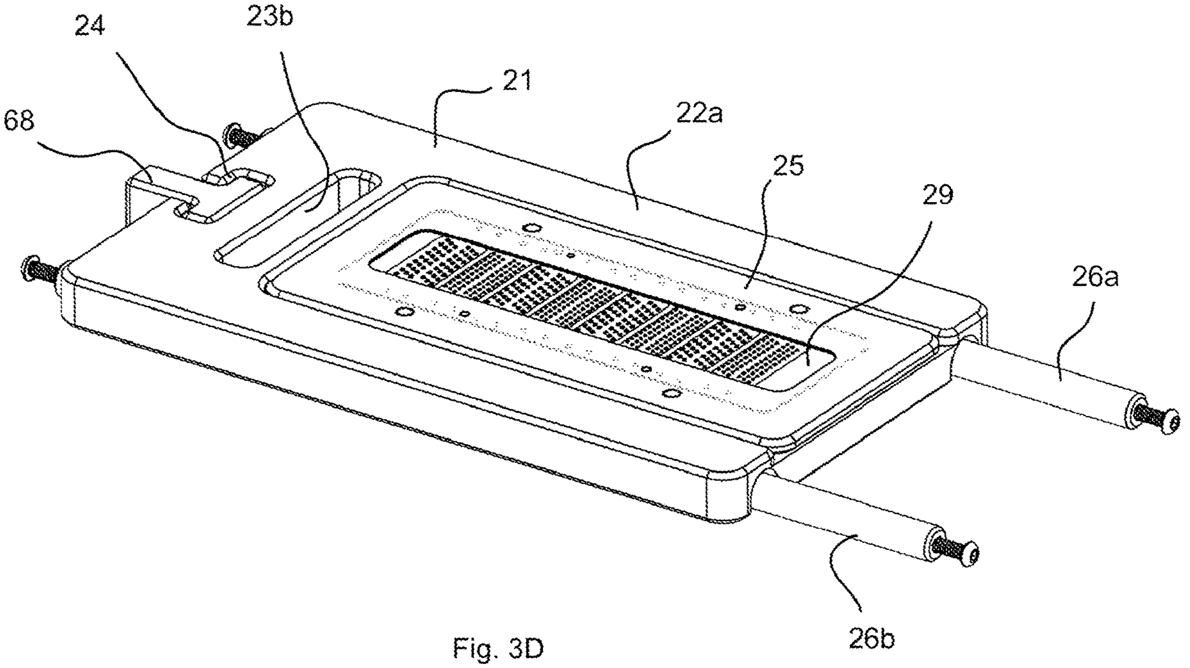

Referring to FIGS. 2A and 2B, the carriage assembly 20 is illustrated in an assembled and exploded configuration, respectively. As illustrated in FIGS. 3A-3C, the carriage assembly 20 comprises a carrier plate 21 that is designed to hold at least one blade. The carrier plate 21 has a top surface 22*a* and bottom surface 22*b* that are generally opposed to each other. The carrier plate 21 also includes at least one opening 23*a* extending through it to permit the bone fibers to fall though it. The carrier plate 21 can also include one or more handles or handle openings 23*b* extending into or through it to permit a user to safely handle or remove the carrier plate 21 from the apparatus 10.

As illustrated in FIGS. 2B and 3A-3C, the carrier plate 21 is configured to mate with a portion of the drive assembly 60. In one example embodiment, the carrier plate 21 comprises at least one channel or notch 24 formed into it that is configured to mate with a portion of the drive assembly 60. The channel 24 is positioned near an end of the carrier plate 21 proximate to the housing 13. The at least one channel 24 ideally has a size and shape that corresponds to a size and shape of the mating/coupling portion of the drive assembly 60.

Referring back to FIGS. 2A and 2B, the carriage assembly 20 also comprises one or more rails 26*a* and 26*b* that are positionable in channels or grooves 28*a* and 28*b* formed in the bottom surface 22*b* of the carrier plate 21. The rails 26*a* and 26*b* support and guide the carrier plate 21 as it reciprocates during the production process. The rails 26*a* and 26*b* may have any cross-sectional shape, such as circular or square, provided that the carrier plate 21 is able to slide or move along their length. The channels or grooves 28*a* and 28*b* can have a surface able to mate with the rails 26*a* and 26*b*.

Referring to FIG. 2B, the carriage assembly 20 also comprises a replaceable fiber cutting plate or blade 29 configured to cut a donor bone material into fibers of varying physical characteristics. The fiber cutting plate 29 is mounted or positioned either on the top surface 22*a* or the bottom surface 22*b* of the carrier plate 21. As illustrated in FIG. 4A, the fiber cutting plate 29 includes a first plurality of blades 30*a* having a first cutting characteristic and a second plurality of blades 30*b* having a second cutting characteristic, whereby the first plurality of blades 30*a* and the second plurality of blades 30*b* create a composition of bone fibers having at least two different dimensional characteristics. The fibers of the present invention utilizing at least two different dimensional characteristics to create implants having properties (e.g., pore formation and sizes) that mimic native bones.

The fiber cutting plate 29, combined with the capabilities of the actuator assembly 12, form a system 10 that can cut bone fibers having at least two or more dimensions. In one example embodiment of the present invention, there are a first plurality of blades 30*a* extending upwardly from an upper surface of the fiber cutting plate 29. There are also a second plurality of cutting blades 30*b* extending upwardly from the upper surface of the fiber cutting plate 29. The first plurality of cutting blades 30*a* have a height and width, when measured from the upper surface of the fiber cutting plate 29, then the plurality of second cutting blades 30*b*. The variation in the height and width of the first cutting blades 30*a* and the second cutting blades 30*b* provide bone fibers of at least two different thicknesses and two different widths.

In an example embodiment of the present invention, the placement of the cutting blades on the fiber cutting plate 29, along with a variation of stroke length, can add another dimensional difference to the bone fibers. For instance, the first plurality of cutting blades 30*a* are positioned and arranged proximate to one end of the fiber cutting plate 29 and the second plurality of cutting blades 30*b* are oriented generally toward a second end of the fiber cutting plate 29. Each of the first plurality of blades 30*a* and each of the second plurality of blades 30*b* have an adjacent opening, 32*a* and 32*b* respectively, which permit the cut fibers to pass through the fiber cutting plate 29.

Figure 4C:
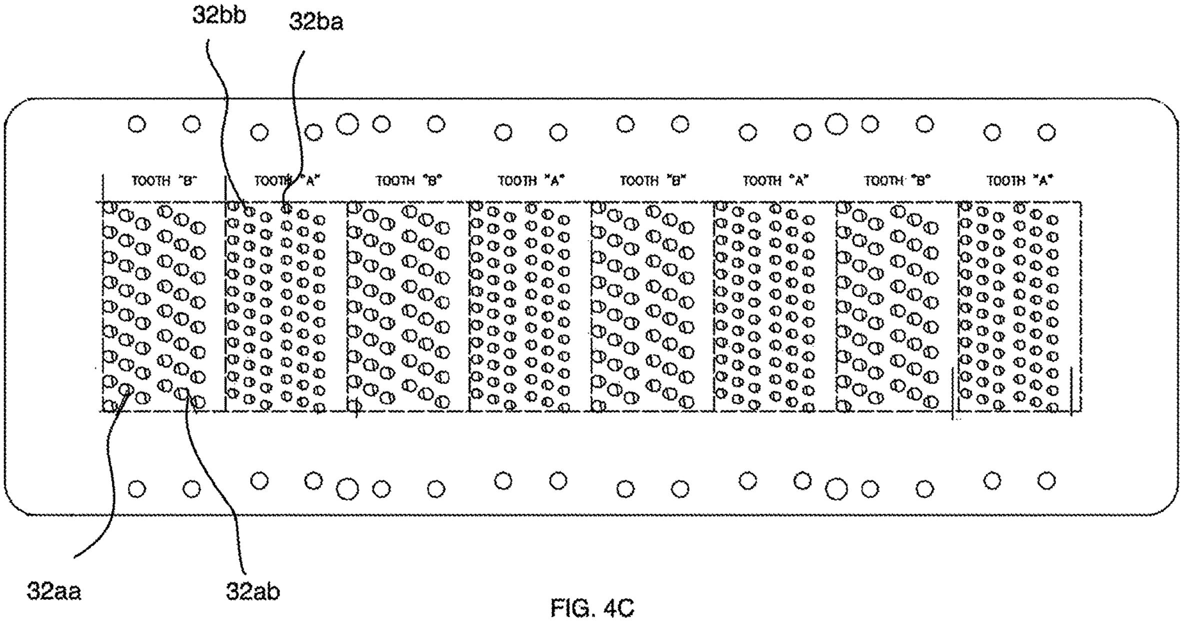
FIG. 4C is a top view of a fiber cutting plate having zones of blades for a fiber producing apparatus that is configured to make fibers having at least two-dimensional characteristics.

In another example embodiment, as illustrated in FIG. 4C, the first plurality of blades 30*a* and the second plurality of blades 30*b* are orientated facing each other such that the first plurality of cutting blades 30*a* cuts the donor bone on a first out-stroke and the second plurality of cutting blades 30*b* cut the bone on a second or in-stroke. A difference in the length of the first stroke and the second stroke creates bone fibers having different lengths.

In another example embodiment, as also illustrated in FIG. 4C, the first plurality of blades 30*a* and the second plurality of blades 30*b* are oriented in an alternating fashion and orientated in an opposite direction to an adjacent cutting blade. Such that the first plurality of cutting blades 30*a* cuts the donor bone on a first or out-stroke and the second plurality of cutting blades 30*b* cuts the donor bone on a second or in-stroke. As described above, a difference in the length of the first stroke and the second stroke can create bone fibers having different lengths.

The same cutting blades 30*a* or 30*b* can also alternate directions such that the fiber cutting plate 29 has multiple cutting zones. This is illustrated by cutting blades 30*aa*, 30*ab* and 30*bb*, 30*ba*. Any number of zones and alternating cutting blade rows can be implemented.

A particular advantage of the present invention is that the alternating cutting direction of the cutting blades 30*a*, 30*aa*, 30*ab*, 30*b*, 30*bb*, and 30*ba*, enables cutting or severing of created fibers from the donor bone in both stroke directions (strokes occurring in the X-plane parallel to a horizontal table surface). The ability to cut or sever the fibers from the donor bone enables the ability to vary a bone fiber length by adjusting one or more stroke lengths.

The ability to cut or sever the bone fibers in both stroke directions in the X-plane can be improved by a weight or pressure provided in a Z-plane direction, which causes a compression of the bone against the fiber cutting plate 29. The weight or pressure may be adjusted to increase or decrease the Z-directional force. As a bone fiber is pulled out of a cutting blade (e.g., 30*aa*) hole or aperture it can expand and as the weight in the Z-plane causes a downward force it causes the attached bone fiber it to engage a cutting blade (e.g., 30*ab*) that is oriented in an opposition direction, thereby causing it to be severed from the donor bone.

Figure 4D:
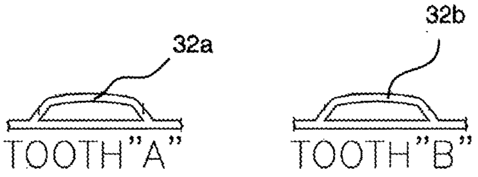
FIG. 4D is a side view of a different cutting blades of the fiber cutting plate for a fiber producing apparatus that is configured to make fibers having at least two-dimensional characteristics.

As illustrated in FIGS. 4B and 4D, the cutting blades 30*a*, 30*aa*, 30*ab*, 30*bb*, 30*ba* can have arcuate or pointed upper surfaces generally opposite the cutting plate 29 top surface. The arcuate or pointed shapes of the cutting blades, 30*a*, 30*aa*, 30*ab*, 30*b*, 30*bb*, and 30*ba* enable them to cut the bone fibers more easily as well as to aid in severing the bone fibers from the donor bone.

The fiber cutting plate 29 is removably positioned on the carrier plate 21 to aid in cleaning, sterilization, and replacement. The fiber cutting plate 29 may mate with one or more pins 26 extending from the carrier plate 21. In another example embodiment, fasteners are used to secure the fiber cutting plate 29 to the carrier plate 21.

In one example embodiment of the present invention, as illustrated in FIG. 2B, a single more securing member 25 is used to secure the fiber cutting plate 29 to the carrier plate 21. The securing member 25 comprises a generally planar frame having an opening 27 extending through it. The opening 27 is aligned with the cutting blades 30*a*, 30*aa*, 30*ab*, 30*b*, 30*bb*, and 30*ba* of the fiber cutting plate 29. The fiber cutting plate 29 is placed between the securing member 25 and the carrier plate 21 and then fastened in placed by one or more fasteners.

Figure 5:
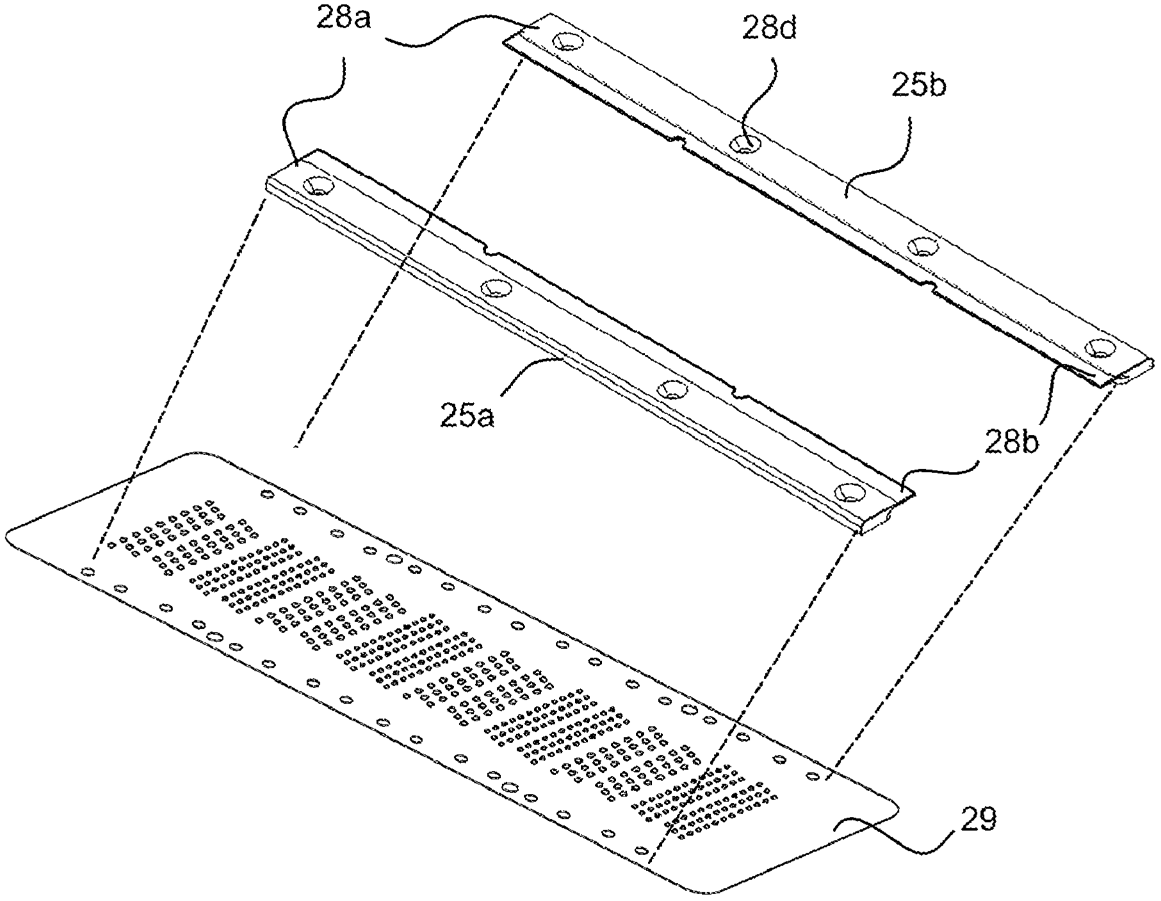
FIG. 5 is a perspective view of a fiber cutting plate and securing members for a fiber producing apparatus that is configured to make fibers having at least two-dimensional characteristics.

In another example embodiment, as illustrated in FIG. 5, the fiber cutting plate 29 is held in place on the carrier plate 21 by one or more securing members 25*a* and 25*b* comprising elongate bars having a thicker track portion 25*c* and a generally thinner flange or tapered edge portion 25*d*. The track portion 25*c* is used as a slide and/or spacer and the flange portion 25*d* extends over an edge of the fiber cutting plate 29 securing it in place. Fasteners can be used to fasten the securing members 25*a* and 25*b* to the fiber cutting plate 29. Fasteners are extendable through one or more openings 25*e* extending through the securing members 25*a* and 25*b*.

As illustrated in FIGS. 1A-2B, the carriage assembly 20 is selectively covered by a top plate 40 having an upper surface 41*a* and a lower surface 41*b*. The upper surface 41*a* includes a bone containment portion 42 extending therefrom that is positioned over an opening 43 extending through the top plate 40 and the containment portion 42. The containment portion 42 is configured to receive and hold the donor bone. In one example embodiment, the top plate 40 includes one or more tabs 44*a*, 44*b*, and 44*c* that are configured to mate with the support assembly 80 to removably secure the top plate 40 in place. Fasteners can be used to secure the top plate 40 in place.

As can be seen in FIG. 2B, the opening 43 of the containment portion 42 is aligned with the opening 27 of the securing member 25, whereby the cutting blades 30*a*, 30*aa*, 30*ab*, 30*b*, 30*bb*, and 30*ba* fiber cutting plate 29 are exposed through the openings.

A plunger assembly 50 configured to hold the donor bone in the containment portion 42 is adjustably positioned above the top plate 40. The plunger assembly 50 comprises a pressure plate 52 and a press guide 54. The pressure plate 52 is configured to transfer pressure along the Z axis through the press guide 54 and onto the donor bone to generally fix the position of the donor bone in the containment portion 42 of the top plate 40.

In one example embodiment of the present invention, the press guide 54 comprises a toothed free end or surface that can pierce into the donor bone to fix it in place. The press guide 54 has a shape and configuration that enables to mate or extend into the containment portion 42 of the top plate 40. The press guide 54 may also be able to extend into the opening 27 of the securing member 25 as the donor bone draws near completion of its processing.

The top plate 40 and the pressure plate 52 have one or more holes 56*a* and 56*b*, respectively, extending through them. The holes 56*a* and 56*b* are aligned and configured to receive and slide over one or more guides 58*a*, 58*b*, and 58*c* coupled to and extending generally upward from the carriage assembly 20.

As mentioned above, the present invention includes a drive assembly 60 that is operatively coupled to the carrier plate 21 of the carriage assembly 20. The drive assembly 60 comprises a motor 61 coupled to a reciprocating drive shaft 62 that is operatively coupled to the channel 24 of the carrier plate 21. The motor 61 moves the drive shaft 62 and correspondingly the carrier plate 21 in a reciprocating motion along the X axis.

Figure 6A:
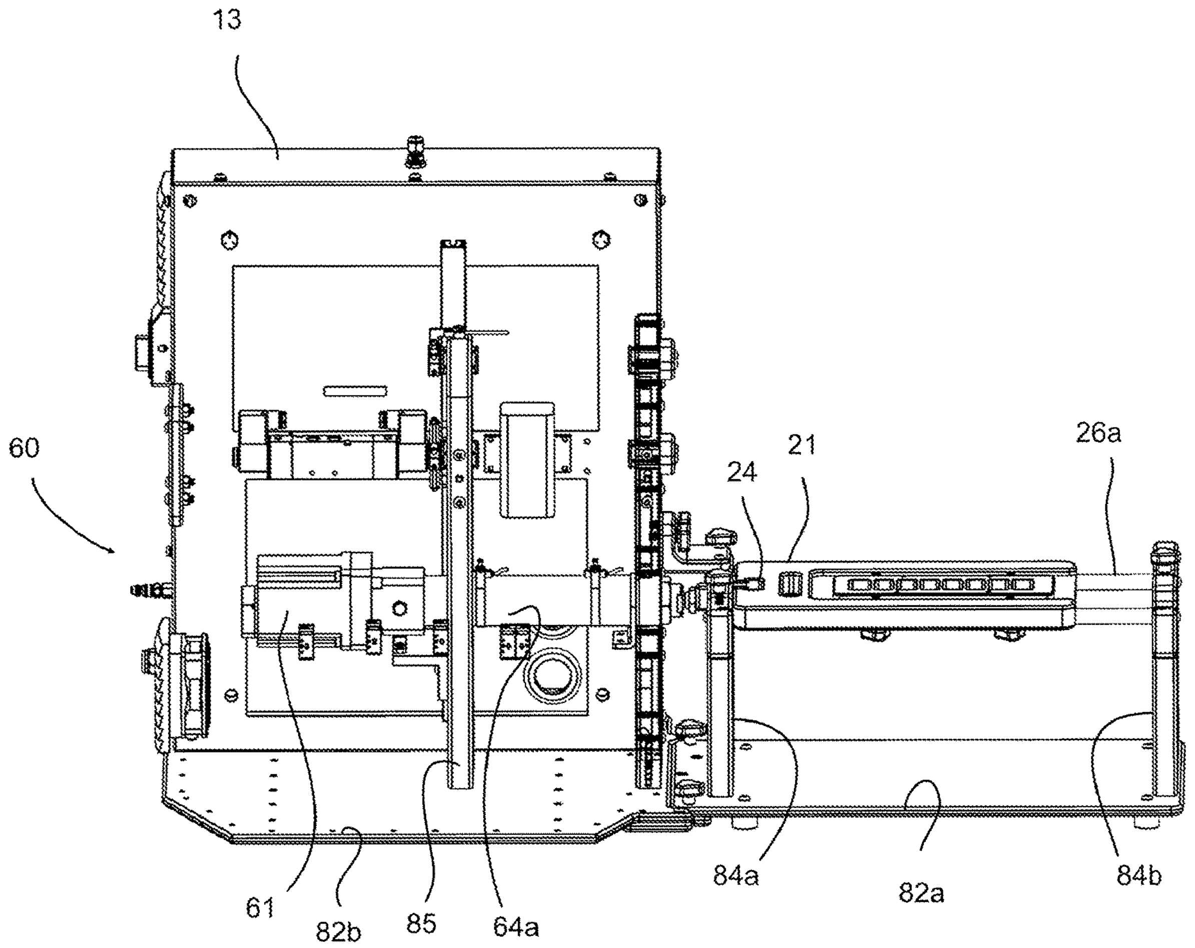
FIG. 6A is a front view of a motor in a housing configured to move the carriage assembly for a fiber producing apparatus that is configured to make fibers having at least two-dimensional characteristics.
Figure 6B:
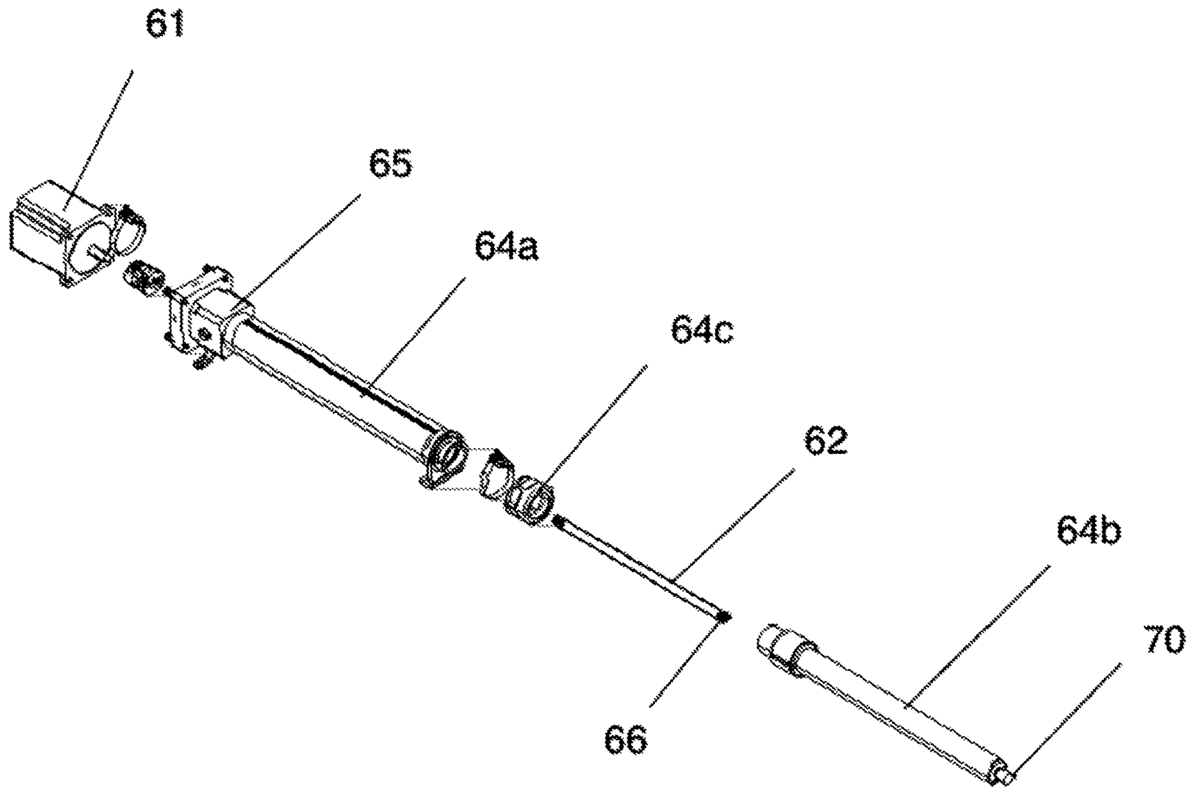
FIG. 6B is an exploded perspective view of a drive assembly coupled to the motor and configured to drive the carriage assembly of an apparatus for making fibers having at least two characteristics according to an example embodiment of the invention.

In one example embodiment of the present invention, as illustrated in FIG. 6B, the drive shaft 62 can be positioned in a drive sleeve 64*a*. The drive sleeve 64*a* can include a sub-sleeve 64*b* that at least partially encloses and travels with the drive shaft 62 while it moves between its reciprocating strokes. The drive sleeve 64*a* and sub-sleeve 64*b* can be coupled together by a fastener 64*c* that is able to seal at least the interior of the drive sleeve 64*a*. The motor 61 and the drive shaft 62 can be directly coupled together or can be coupled together by a gear mechanism 65 that translates the rotational movement of the motor 61 to the reciprocating movement of the drive shaft 62. An end 66 of the drive shaft 62 can be coupled to the carrier plate 21 or coupled to a coupler 68 (see FIG. 3C) that is operatively coupled or nested in the opening or channel 24 of the carrier plate 21. In another example embodiment of the present invention, as illustrated in FIG. 6B, the sub-sleeve 64*c* includes a drive end 70 that is either directly coupled to the carrier plate 21 or to the coupler 68, which is in turn coupled to the carrier plate 21.

Referring back to FIGS. 1A-2B, the carriage assembly 20 can be supported by a support assembly 80 that positions the carriage assembly 20 a distance above table or floor surface. As illustrated in FIG. 1A, the support assembly 80 comprises at least one bottom support 82*a* that is positionable on the floor or table surface. One or more upright support members 84*a* and 84*b* extend generally upward from a top surface of the bottom support 82*a*. The carriage assembly 20 can be removably coupled to and supported by the upright members 84*a* and 84*b*.

In another example embodiment, there can be two bottom supports, bottom support 82*a* positioned under at least a portion of the carriage assembly and support bottom 82*b* positioned at least partially under the drive assembly 60. The bottom supports 82*a* and 82*b* can be manufactured of different materials. For instance, bottom support 82*a* can be manufactured from a vibration reducing material, such as rubber, that reduces or absorbs any vibrations generated by the drive assembly 80. Bottom support 82*b* can be manufactured from any material, such as steel, that can be easily cleaned and sterilized after being in contact with the bone fibers. Similarly, the upright support members 84*a* and/or 84*b* can also be manufactured from similar or dissimilar materials that aid in stabilizing the system 10 and/or aid in cleaning the system 10. Various materials can be used and should be considered to be within the spirit and scope of the present invention.

A motor upright member or stand 85 can also be coupled to or mounted on the bottom support 82*b*. The motor upright member 85 is configured to position the motor 61 at a height that positions the drive shaft 62 parallel to the bottom supports 82*a* and 82*b*.

In one embodiment of the invention, the motor upright member 85 is adjustable to accommodate systems 10 of varying sizes. A height of the upright members 84*a* and 84*b* can also be adjustable to accommodate systems 10 of various sizes. The bottom support members 82*a* and 82*b* can be configured to permit various placement locations of the upright support members 84*a* and 84*b*. Varying the distance between the upright support members 84*a* and 84*b* adjusts a distance or space between the upright support members 84*a* and 84*b*. Additional upright support members can be added to the system 10 to accommodate drive shafts 62 and carriage assemblies 20 of varying lengths.

Figure 7:
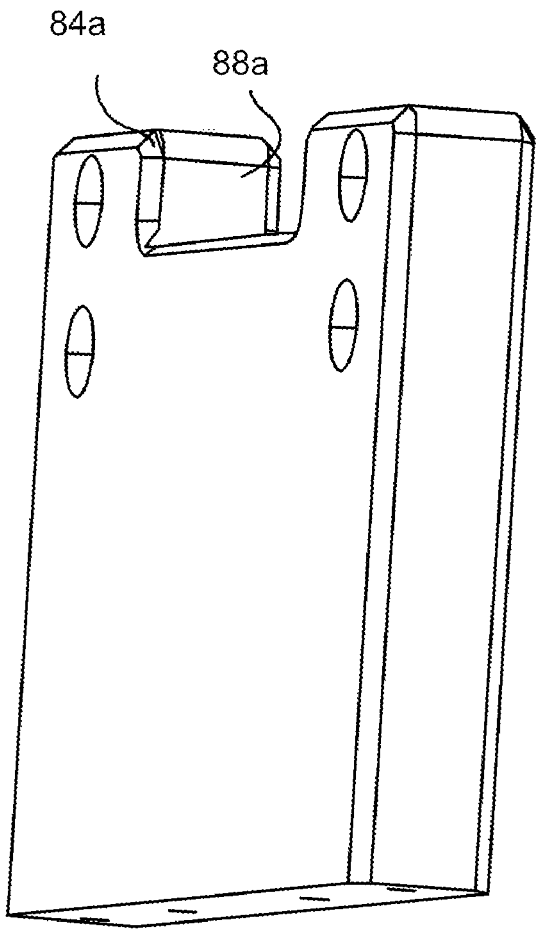
FIG. 7 is a perspective view of a portion of the support assembly of an apparatus for making fibers having at least two characteristics according to an example embodiment of the invention.

As illustrated in FIG. 7, upright member 84*a*, which is positioned generally closer to the drive assembly 60, includes at least one recess formed therein to receive and support drive shaft 62 and/or sub-sleeve 64*b*. The at least one recess or cradle 88*a* formed in it and extending through its opposed planar surfaces. The at least one recess 88*a* has a size and shape configured for receiving and supporting the drive shaft 62 and/or the sub-sleeve 64*b*. The at least one recess 88*a* can also be generally larger than a diameter of the drive shaft 62 and/or the sub-sleeve 64*b* to allow for free reciprocating movement of the drive shaft 62 and/or the sub-sleeve 64*b* when processing the donor bone.

Figure 8:
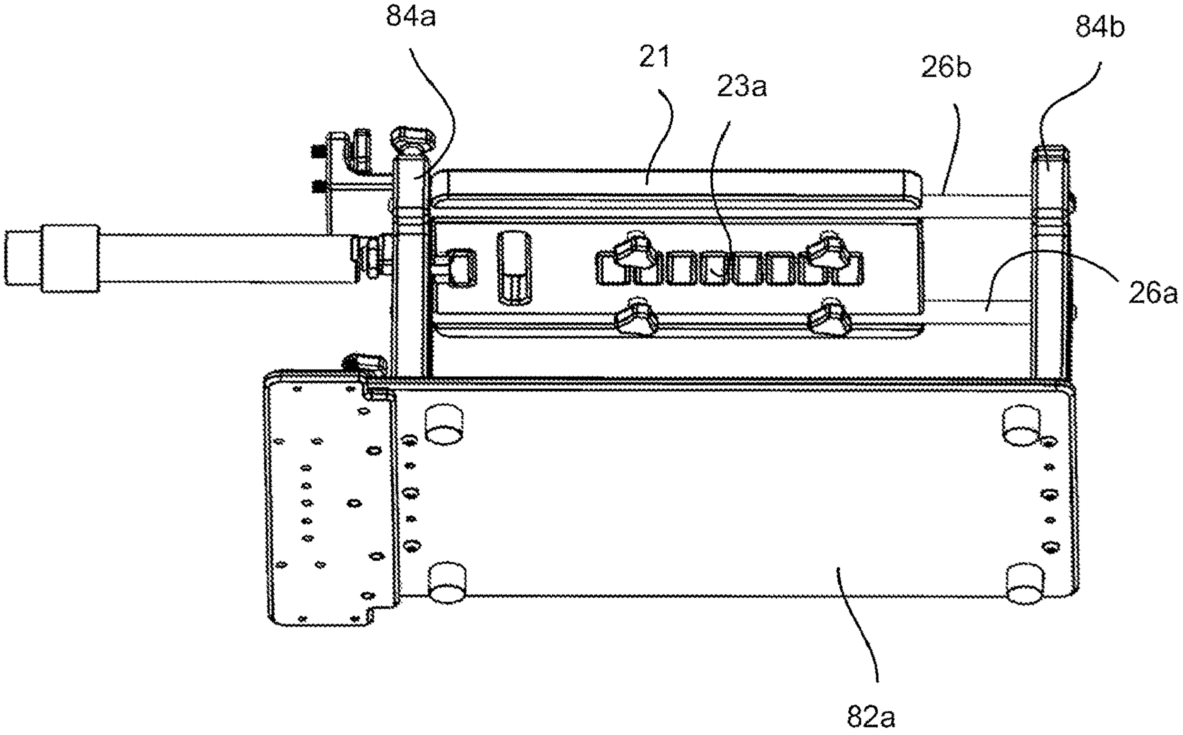
FIG. 8 is a perspective view of the carriage assembly of an apparatus for making fibers having at least two characteristics according to an example embodiment of the invention.
Figure 9A:
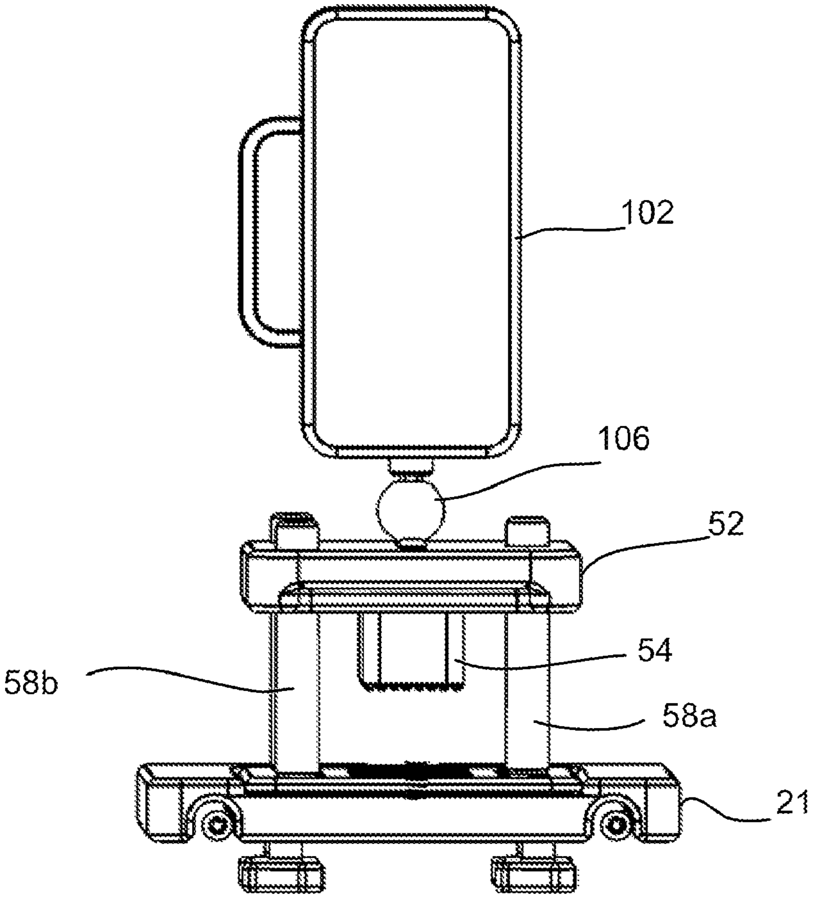
FIG. 9A is a front view of a press assembly disposed on the carriage assembly of an apparatus for making fibers having at least two characteristics according to an example embodiment of the invention.
Figure 9B:
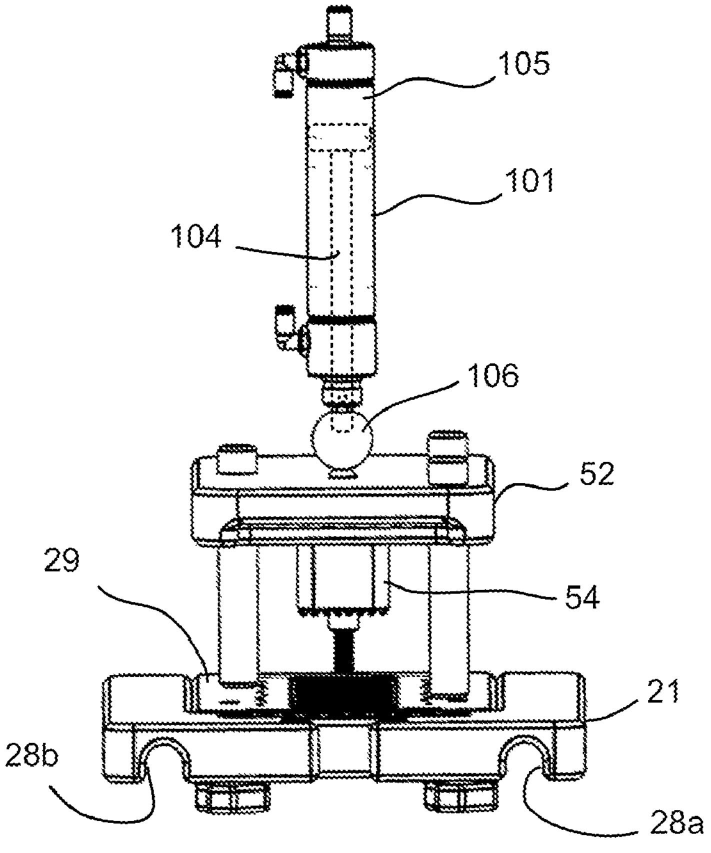
FIG. 9B is a front view of a press assembly showing a rod in dashed lines, the rod disposed on the carriage assembly of an apparatus for making fibers having at least two characteristics according to an example embodiment of the invention.

As illustrated in FIGS. 8, rails 26*a* and 26*b* extend between the spaced upright support members 84*a* and 84*b*. The rails 26*a* and 26*b* can be coupled to the upright support members 84*a* and 84*b* by fasteners or they can be nested into seats formed into the planar surfaces of the upright support members 84*a* and 84*b*. The rails 26*a* and 26*b* are generally spaced apart and positioned on each side or long side of the opening 23*a* of the carrier plate 21 to allow for the bone fibers to freely pass through.

Referring to FIGS. 1A and 1B, the apparatus 10 of the present invention also comprises a bone press assembly 100 that can hold and press the donor bone against the fiber cutting plate 29 as the plate 29 moves between its reciprocating strokes. The bone press assembly 100 comprises a piston 101 positioned in a press housing 102. In one example embodiment, as illustrated in FIGS. 1A and 1B, the bone press assembly 100 comprises a double acting piston 101 configured for applying and retracting pressure onto the pressure plate 52. The piston 101 comprises a rod 104 slidably positioned within a barrel 105.

An end of the rod 104 is coupled to a ram 106 that is configured for pressing against the pressure plate 52. In one example embodiment of the present invention, the ram 106 has a generally spherical shape. However, the ram 106 may have any size and shape configured to exert pressure onto the pressure plate 52.

The rod 104 of the piston 101 is extendable to exert pressure on the pressure plate 52 and retractable to relieve pressure from the pressure plate 52. As illustrated in FIGS. 1A and 1B, the movement of the rod 104 is controlled by a hydraulic system that comprises a pump 110 located in the housing 13. The pump 110 is in fluid communication with the piston 101 by one or more hoses 112 or similar conduits. The hoses 112 care positioned in one or more support arms 120 that are coupled to and extending between the housing 13 and the bone press assembly 100.

Figure 10A:
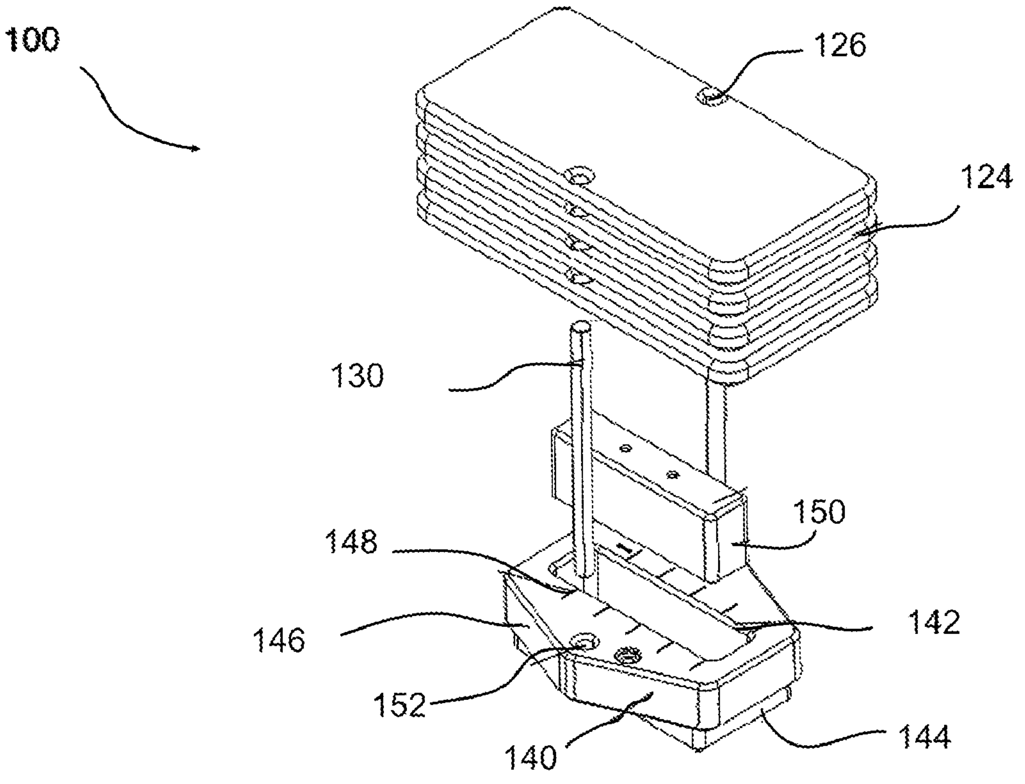
FIG. 10A is an exploded view of a manual press assembly of an apparatus for making fibers having at least two characteristics according to an example embodiment of the invention.

Pressure can also be applied to the pressure plate 52 by a manual mechanism. As illustrated in FIG. 10A, a manual mechanism comprises one or more weights 124 that are positionable over one or more guides 130. The weights 124 can be added to exert more pressure or removed to relieve pressure. The weights 124 can contact either the pressure plate 52, press guide 54, or the containment portion 42. In another example embodiment of the present invention, a lever mechanism may be employed to apply pressure to the donor bone.

Figure 10B:
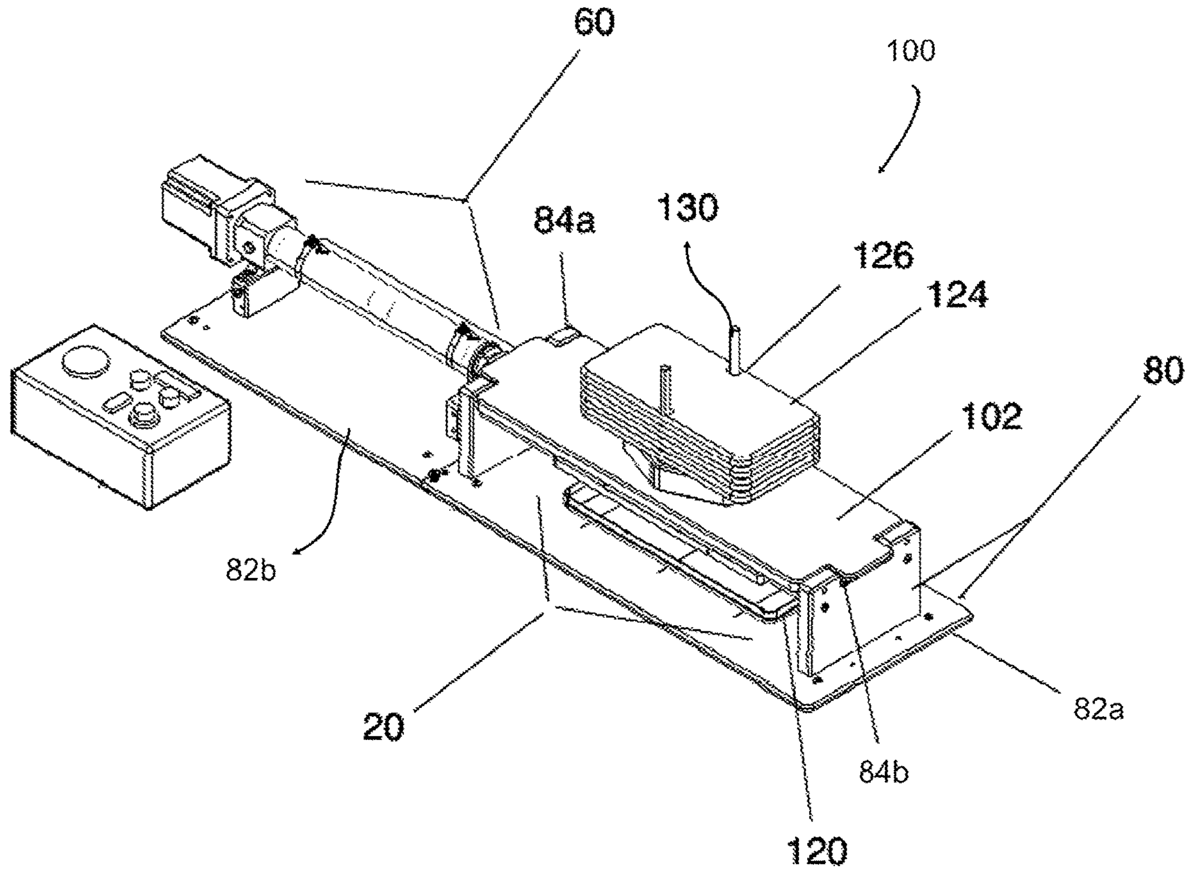
FIG. 10B is a perspective view of an apparatus for making fibers having at least two characteristics according to an example embodiment of the invention.
Figure 10C:
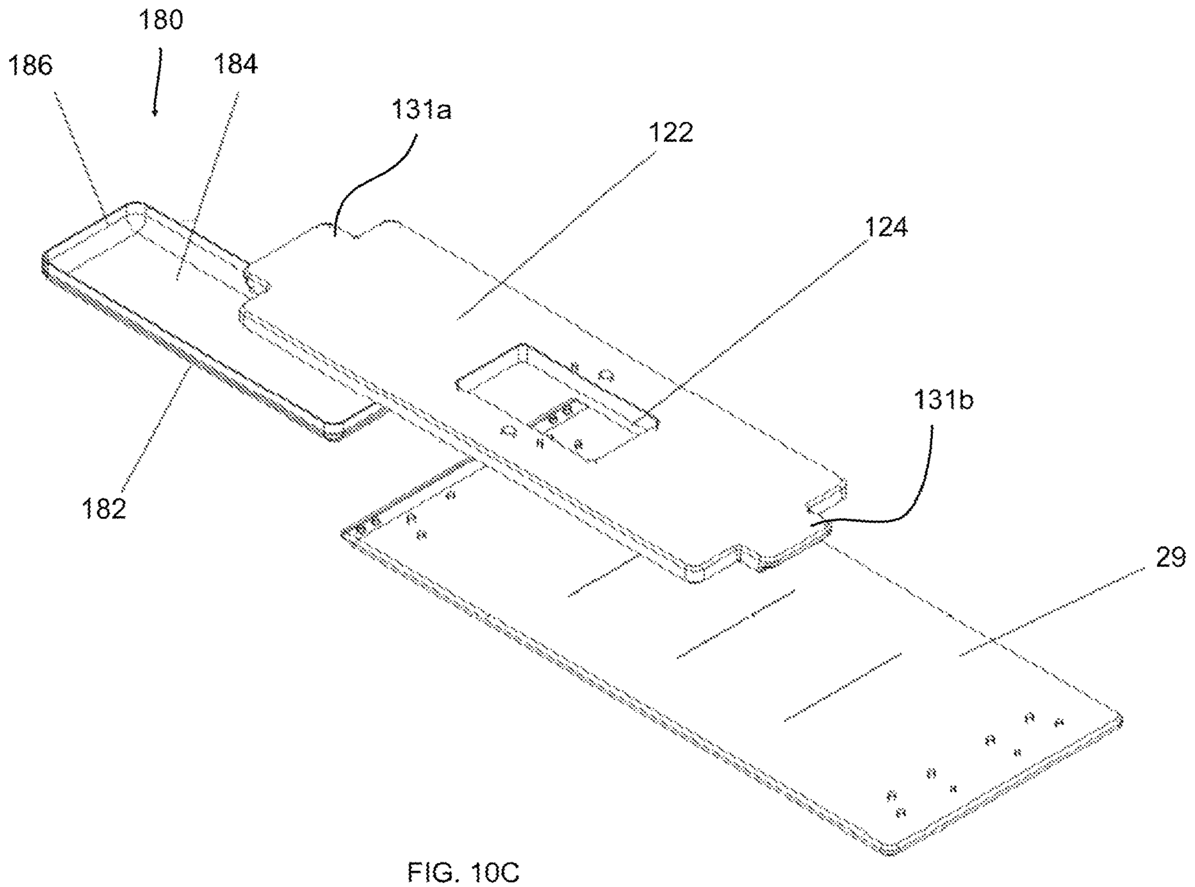
FIG. 10C is an exploded view of a collection assembly configured to catch the fibers having at least two-dimensional characteristics for use with an apparatus for making fibers having at least two characteristics according to an example embodiment of the invention.

In an alternative fiber formation apparatus 100, as illustrated in FIGS. 10A-10C, a press support plate 122 is provided having a hole 104 extending through its generally parallel opposed surfaces. The hole 104 is generally aligned or in-register with the opening 23*a* of the carrier plate 21. The press support plate 122 comprises at least two tabs 131*a* and 131*b* that are supported or coupled to the support members 84*a* and 84*b*.

In one example embodiment of the invention, the tabs 131*a* and 131*b* of the press support plate 122 can be formed as handles that can be coupled to or rested upon the upright support members 84*a* and 84*b*.

The bone press assembly 100 also comprises a bone housing or containment 140 having an aperture 142 extending generally through its center to provide access to the fiber cutting plate 29. As illustrated in FIG. 10A, the bone housing 140 includes an extension portion or wall 144 extending downwardly from a lower surface of the bone housing 140. The extension portion 144 extends about the aperture 142. The extension portion 144 has a height generally less than a thickness of the press support plate 122 and the carrier plate 21 such that the extension portion 144 terminates short of engaging the fiber cutting plate 29.

As illustrated in FIG. 10A, the bone housing 140 can include a collar portion 146 extending outwardly from or generally perpendicular to the extension portion 144 to act as a stop and control the depth of the extension portion 144 in the opening 23*a* of the carrier plate 21 and the hole 124 of the press support plate 122. A top surface of the bone housing 140 can include one or more indicia 148 formed or placed thereon. The indicia, as shown by numeral 148, can comprise a line or other marking denoting a predetermined length, width, or thickness. The measurements are used to ensure proper formation of bone fibers having different physical characteristics or dimension. For example, the length measurement can be used to measure a length of bone donor placed in the bone housing 140. The length can be used to calculate a particular first stroke length and a particular second stroke length. The measurement of the stroke lengths are used to insure bone fibers of different lengths. The indicia 148 can take any shape or form. For instance, a numerical indicia can be placed or formed on the bone housing 140 instead of or in addition to tics, dashes, and the like.

The press assembly 100 also comprises a plunger 150 that is configured for being inserted into the aperture 142 of the bone housing 140. The plunger 150 includes a generally textured lower surface that is configured to engage the donor bone material and reduce its movement within the aperture 142 of the bone housing 140. The lower surface of the plunger 150 may comprise a plurality of patterned projections that are configured to penetrate the periosteum connected to the donor bone, thereby firmly resisting loss of grip, and thus loss of relative motion, between cutting plate 29 and the donor bone material.

The lower surface of the plunger 150 can also include a plurality of teeth capable of engaging with the surface of the donor bone material or periosteum. Other textured configurations are also possible and should be considered to be within the spirit and scope of the invention.

The weights 124 are also provided to exert downward pressure on the plunger 150 causing it to engage with the surface of the donor bone, thereby causing it to be pressed against the cutting blades 30*a* and 30*b* of the fiber cutting plate 29. The weights 124 can include one or more holes 126 extending through them and are able to receive and move along one or more poles or pins 130. The poles 130 act as a guide for the one or more weights 124. In one example embodiment of the invention, the poles 130 can extend through the one or more holes 152 in the bone housing 140. The poles 130 can also extend into the upper or top surface of the press support plate 122. The passage of the poles 130 through the weights 124, the bone housing 140 and, optionally, the press support plate 122, provides precise uniform movement of the weights 124 onto the plunger 150 and engagement of the donor bone onto the fiber cutting plate 29.

In use, an operator places a donor bone in the containment portion 42 or a similar retaining member. The apparatus 10 or 100 is switched from an off-state to an on-state. An emergency button is checked to ensure it is deactivated prior to performing the fiber cutting process. An actuator control is activated to begin the fiber cutting process. In one example embodiment, two actuator controls are required to be activated to ensure an operator's hands are free from the cutting area.

An operator is than able to activate the plunger assembly 50, which moves the rod 104 and ram 106 toward the pressure plate 52. The press, plunger, or guide 54 is then pressed against the donor bone, which is pressed against the fiber cutting plate 29. The textured surface of the press guide 54 penetrates the periosteum, thereby firmly resisting a loss of grip, and thus a loss of relative motion between fiber cutting plate 29 and the donor bone.

The operator can then begin the fiber cutting process by activating the motor 61 that is operatively coupled to the carriage assembly 20. The motor 61 moves the carriage assembly 20, including, the fiber cutting plate 29 and its blades 30*a*, 30*aa*, 30*ab*, 30*b*, 30*bb*, and 30*ba*, in a reciprocating motion. The blades 30*a*, 30*aa*, 30*ab*, 30*b*, 30*bb*, and 30*ba* cut fibers having dimensions consistent with the dimensions of the blades 30*a*, 30*aa*, 30*ab*, 30*b*, 30*bb*, and 30*ba*, the length of the strokes of the movement of the carriage assembly 20, and the amount of pressure applied to the donor bone against the cutting plate 29. As the donor bone is cut, grated, or shredded, the pressure or weight continues to increase, thereby pushing the donor bone against the fiber cutting plate 29 until the donor bone reaches a predetermined minimum thickness. Once the predetermined minimum thickness is reached the apparatus 10 or 100 stops and an operator can remove any remaining donor bone from the containment portion 42.

As fibers having different dimensions are cut, they can fall into a collection assembly 180, as illustrated in FIG. 10C. The collection assembly 180 comprises at least a container 182 having an interior 184 and a peripheral wall 186. The container 182 is removably positionable on the bottom support 82*a* under the carrier plate 21 and the fiber cutting plate 29. The bone fibers can be removed from the container 182 and either placed through a post-process or packaged for sale.

The apparatus 10 or 100 of the present invention includes, but is not limited to, the following controls. 1) a first stroke-length control, a second stroke-length control, a speed control, a weight or pressure control, a depth control, and the like. The apparatus 10 or 100 can display parameters (such as those of the listed control) on the display 15. Other parameters can also be displayed and should be considered to be within the spirit and scope of the invention.

The first stroke and the second stroke of the apparatus 10 and 100 can be set to create varying lengths of bone fibers. For instance, the first or outward stroke can be set to 3 mm while the second or inward stroke can be set to 1 mm. As described above, the first plurality of cutting blades 30*a* can have a height and/or width different than the second plurality of cutting blades 30*b*. As a result, bone fibers having varying lengths and different thicknesses and/or widths are produced. Different blades 30*a*, 30*aa*, 30*ab*, 30*b*, 30*bb*, and 30*ba* with different cutting blade configurations can be used to make or create a greater variety of bone fibers. The different blades 30*a*, 30*aa*, 30*ab*, 30*b*, 30*bb*, and 30*ba* can be arranged in different areas or zones. The blades 30*a*, 30*aa*, 30*ab*, 30*b*, 30*bb*, and 30*ba* can also be arranged in zones facing each other, as particularly illustrated in FIG. 4D. This type of arrangement of the blades 30*a*, 30*aa*, 30*ab*, 30*b*, 30*bb*, and 30*ba* ensures that a fiber cut in one direction, that has not been severed, is severed by the opposite blade prior to beginning the cutting of another fiber. The arrangement ensures consistency in the variation of the fiber composition.

The apparatus 10 or 100 can be preprogrammed to vary stroke lengths and the pressure applied to the donor bone. In one example embodiment, the stroke lengths and pressures can be randomly varied throughout the cutting process to provide a fiber composition that is completely random and provides a potentially more realistic or natural fibrous consistency.

While the invention has been disclosed as cutting, shredding, or grating donor bone material it is within the spirit and scope of the invention that any material that can be cut, shredded, or grated can be used in the apparatus 10 or 100 of the present invention.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. An example of this would be accomplishing relative motion between the cutting blade and bone other than reciprocating linear motion by deploying a rotational design where the bimodal cutting teeth travel in a circular path and the bone shaft is held in contact with the blade with a variable amount of force to produce a fiber. Moreover, features or aspects of various example embodiments may be mixed and matched (even if such combination is not explicitly described herein) without departing from the scope of the invention.

What is claimed is:

1. A method of producing fibers from a donor bone, the method comprising:

forming fibers by cutting the donor bone with a cutting plate comprising a first plurality of blades having a first width and a second plurality of blades having a width different from the first plurality of blades;

moving the cutting plate in a first stroke having a first length and then in a second stroke having a second length different from the first length; and wherein at least two of the formed fibers comprise a different length and width.

2. The method of producing fibers according to claim 1, further comprising the step of collecting the fibers below the cutting plate.

3. The method of producing fibers according to claim 1, further comprising the step of combining the fibers with an aqueous solution to form a moldable material.

4. The method of producing fibers according to claim 3, further comprising the step of drying the moldable material to retain a molded configuration.

5. The method of producing fibers according to claim 1, further comprising the step of applying a first pressure upon the donor bone being cut and then applying a second pressure different from the first pressure on the donor bone being cut, wherein a difference between the first pressure and the second pressure forms at least two additional fibers comprising different thicknesses.

6. The method of producing fibers according to claim 5, further comprising the step of sandwiching the donor bone between a press and the moving cutting plate.

7. An apparatus for producing fibers from a donor bone, the apparatus comprising:

a cutting plate comprising a first plurality of blades having a first width and a second plurality of blades having a width different from the first plurality of blades;

a motor operatively coupled to the cutting plate to move the cutting plate in a first stroke having a first length and then in a second stroke having a second length different from the first length; and wherein the apparatus is configured to produce fibers such that at least two of the fibers comprise a different length and width.

8. The apparatus for producing fibers from a donor bone according to claim 7, further comprising a collection container configured to collect the fibers.

9. The apparatus for producing fibers from a donor bone according to claim 7, wherein the fibers are configured to be mixed with an aqueous solution to form a moldable material.

10. The apparatus for producing fibers from a donor bone according to claim 9, wherein the moldable material is configured to be dried by an oven.

11. The apparatus for producing fibers from a donor bone according to claim 7, further comprising a press assembly configured to apply a variable pressure against the donor bone.

12. A method of producing fibers from a donor bone, the method comprising:

forming fibers by cutting the donor bone with a cutting plate comprising a first plurality of blades having a first width and a second plurality of blades having a thickness different from the first plurality of blades;

moving the cutting plate in a first stroke having a first length and then in a second stroke having a second length different from the first length; and wherein at least two of the formed fibers comprise a different length and thickness.

13. The method of producing fibers according to claim 12, further comprising the step of collecting the fibers below the cutting plate.

14. The method of producing fibers according to claim 12, further comprising the step of combining the fibers with an aqueous solution to form a moldable material.

15. The method of producing fibers according to claim 14, further comprising the step of drying the moldable material to retain a molded configuration.

16. The method of producing fibers according to claim 12, further comprising the step of applying a first pressure upon the donor bone being cut and then applying a second pressure different from the first pressure on the donor bone being cut, wherein a difference between the first pressure and the second pressure forms at least two additional fibers comprising different thicknesses.

17. The method of producing fibers according to claim 16, further comprising the step of sandwiching the donor bone between a press and the moving cutting plate.

18. The method of producing fibers according to claim 12, further comprising the step of implanting the fibers in a void in a bone.

19. The method of producing fibers according to claim 12, further comprising the step of implanting the fibers in a void of a medical implant.

20. The method of producing fibers according to claim 12, wherein the first length of the first stroke is 3 mm and the second length of the second stroke is 1 mm.

* * * * *